United States Patent
Blake et al.

(10) Patent No.: US 10,022,057 B1
(45) Date of Patent: Jul. 17, 2018

(54) WEARABLE PHYSIOLOGICAL MONITORING AND NOTIFICATION SYSTEM BASED ON REAL-TIME HEART RATE VARIABILITY ANALYSIS

(71) Applicants: Michael Blake, Denver, CO (US); Rodney Kugizaki, Oro Valley, AZ (US)

(72) Inventors: Michael Blake, Denver, CO (US); Rodney Kugizaki, Oro Valley, AZ (US)

(*) Notice: Subject to any disclaimer, the term of this patent is extended or adjusted under 35 U.S.C. 154(b) by 0 days.

(21) Appl. No.: 15/592,566

(22) Filed: May 11, 2017

Related U.S. Application Data (63) Continuation-in-part of application No. 15/004,345, filed on Jan. 22, 2016, now Pat. No. 9,655,532.

(60) Provisional application No. 62/182,261, filed on Jun. 19, 2015.

(51) Int. Cl.
| | |
|---|---|
| *A61B 5/0468* | (2006.01) |
| *A61B 5/024* | (2006.01) |
| *A61B 5/00* | (2006.01) |
| *A61B 5/0456* | (2006.01) |
| *A61B 5/04* | (2006.01) |

(52) U.S. Cl.
CPC ...... *A61B 5/02405* (2013.01); *A61B 5/04012* (2013.01); *A61B 5/0456* (2013.01); *A61B 5/6831* (2013.01); *A61B 5/7405* (2013.01); *A61B 5/7455* (2013.01); *A61B 5/02438* (2013.01)

(58) Field of Classification Search
CPC .............. A61B 5/0456; A61B 5/02405; A61B 5/02438
See application file for complete search history.

(56) References Cited

U.S. PATENT DOCUMENTS

| | | | |
|---|---|---|---|
| 5,280,792 A | 1/1994 | Leong et al. | |
| 5,411,031 A | 5/1995 | Yomtov | |
| 5,682,901 A | 11/1997 | Kamen | |
| 6,212,427 B1 | 4/2001 | Hoover | |
| 6,480,733 B1 | 11/2002 | Turcott | |
| 7,460,899 B2 | 12/2008 | Almen | |
| 7,664,551 B2* | 2/2010 | Cigaina | A61B 5/02405 607/40 |
| 8,346,349 B2* | 1/2013 | Guttag | A61B 5/02405 600/509 |
| 8,668,644 B2* | 3/2014 | Ong | G06F 19/345 600/301 |

(Continued)

OTHER PUBLICATIONS

Malik, Marek, Heart rate variability, Standards of measurement, physiological interpretation, and clinical use, European Heart Journal (1996) 17, 354-381.

(Continued)

*Primary Examiner* — Kennedy Schaetzle (57) ABSTRACT

Methods, devices, and systems for monitoring heart rate variability (HRV) are presented. The HRV monitoring systems and devices are adapted to give immediate feedback to the subject concerning their current condition and any pertinent changes in their condition. The HRV monitoring systems and devices detect, analyze, and assess HRV against a pre-determined application or user need. They also have the ability to provide real time notifications based on the system's assessment of a user's heart HRV and changes in the HRV.

20 Claims, 8 Drawing Sheets

(56) References Cited

U.S. PATENT DOCUMENTS

| | | | |
|---|---|---|---|
| 9,486,148 B2* | 11/2016 | Hseu | A61B 5/0205 |
| 9,801,552 B2* | 10/2017 | Romesburg | A61B 5/0095 |
| 9,848,784 B2* | 12/2017 | Klepp | A61B 5/02405 |
| 2004/0049120 A1 | 3/2004 | Cao et al. | |
| 2005/0177051 A1 | 8/2005 | Almen | |
| 2005/0251051 A1 | 11/2005 | Pougatchev et al. | |
| 2006/0151210 A1 | 7/2006 | Hirai | |
| 2007/0021815 A1 | 1/2007 | Kaiser et al. | |
| 2008/0045815 A1* | 2/2008 | Derchak | A61B 5/0205 600/301 |
| 2008/0082001 A1 | 4/2008 | Hatlestad et al. | |
| 2010/0049070 A1 | 2/2010 | Kao | |
| 2010/0113889 A1 | 5/2010 | Ghanem | |
| 2010/0125217 A1 | 5/2010 | Kuo | |
| 2010/0174205 A1* | 7/2010 | Wegerif | A61B 5/02405 600/515 |
| 2010/0204597 A1 | 8/2010 | Ghanem et al. | |
| 2010/0274144 A1 | 10/2010 | Hu et al. | |
| 2010/0274308 A1 | 10/2010 | Scott | |
| 2011/0184298 A1 | 7/2011 | De Marchena et al. | |
| 2011/0245633 A1 | 10/2011 | Goldberg | |
| 2011/0270346 A1 | 11/2011 | Frei et al. | |
| 2013/0184517 A1 | 7/2013 | Collier | |
| 2014/0073982 A1 | 3/2014 | Yang et al. | |
| 2014/0135631 A1 | 5/2014 | Brumback | |
| 2017/0273574 A1* | 9/2017 | Wu | A61B 5/02055 |

OTHER PUBLICATIONS

W.-C. Fang et al. Expert Systems with Applications 40 (2013) 1491-1504.

Jongyoon Choi et al, Using Heart Rate Monitors to Detect Mental Stress, 2009 Body Sensor Networks 219-223.

* cited by examiner

| HRV Measurement | Description | Value basis | Applied affects, Primary Threshold, Example applicability |
|---|---|---|---|
| SDNN | Standard deviation of all NN intervals | Time domain, statistical | Time and sampling dependent<br>Absolute value - msec<br>Est high freq variations in heartrate, overall HRV<br>e.g., Effects of pollution |
| RMSSD | Sq root of mean squared differences of successive NN intervals | Time domain, statistical | Time and sampling dependent<br>Absolute value – msec<br>Est of short term components of HRV<br>e.g., Stress |
| SDSD | Std deviation of differences between adjacent NN intervals | Time domain, statistical | Time and sampling dependent<br>Absolute value – msec<br>e.g., Driver fatigue |
| SDANN | Std deviation of averages of NN intevals – 5 minute segments | Time domain, statistical | Time and sampling dependent<br>Absolute value – msec<br>Est of long term components of HRV with<br>Approx correlation to ULF<br>e.g., Cardiac arrhythmia |

FIG. 3A

| HRV Measurement | Description | Value basis | Applied affects, Primary Threshold, Example applicability |
|---|---|---|---|
| TINN | Triangular interpretation of NN integral histogram – base width of triangle | Time domain, geometric | Relative insensitivity to NN intervals Absolute value – msec Good for large time frames e.g., Stress |
| pNNx | NN count divided by total NN interval | Time domain, statistical | Rate of change – percentage e.g., Food allergies |
| VLF | Power in Very low frequency range | Frequency domain, spectral | Absolute value – $M-S^2$ $\leq 0.04$ Hz e.g., Asthma |
| LF | Power in Low frequency range | Frequency domain, spectral | Sensitive to 'stationarity' Absolute value – $M-S^2$ and N.U. (LF Normalized) 0.04 – 0.15 Hz e.g., Stress |

FIG. 3B

| HRV Measurement | Description | Value basis | Applied affects, Primary Threshold, Example applicability |
|---|---|---|---|
| LF/HF | Ratio of LF to HF, indication of distribution of power in frequency domain | Frequency domain, spectral | Sensitive to 'stationarity' Absolute value (also applies to normalized values) e.g., Driver fatigue |
| SD1 | SD of axis of Poincare plot perpendicular to the line of identity | Nonlinear, Scatter plot | Absolute value – msec e.g., lactate threshold |
| SD2 | SD of axis of Poincare plot parallel to the line of identity | Nonlinear, scatter plot | Absolute value – msec |
| SD1/SD1 | Ratio of SD1 to SD2 – indicates level of spread in poincare plot | Nonlinear, scatter plot | Ratio, absolute value e.g., postoperative ischemia |

FIG. 3C

| HRV Measurement | Description | Value basis | Applied affects; Primary Threshold; Example applicability |
|---|---|---|---|
| Hilbert Transform | Use of a HT is described as an analytical approach to enhance spectral analysis | Nonlinear/fractal | Absolute value<br>Extraction of HF and LF coupling components to inhalation<br>e.g., Apnea |
| ApEn | Approximate Entropy determination of variability in periodic events | Non-linear, Entropy | Absolute value<br>e.g., Mood changes, stress, cardiac health |
| SampEn | Sample Entropy | Non-linear, Entropy | Absolute value<br>e.g., fainting, bipolar, cardiac health |
| FuzzEn FuzzMEn | Fuzzy Entropy Fuzzy Measure Entropy | Non-linear, Entropy | Improvements over other entropy methods<br>Absolute value<br>e.g., Cardiac health |

Note: The term "NN" is used in place of RR to emphasize the fact that the processed beats are "normal" beats.

FIG. 3D

Detecting a plurality of consecutive heartbeat related waves using one or more electrodes integrated within the wearable device.
200

Detecting a specific wave characteristic of each heartbeat related wave, of the plurality of consecutive heartbeat related waves.
201

Triggering an event when each specific wave characteristic crosses a trigger point.
202

Recording a time value for each event.
203

Determining and recording an interval for each time value to generate a temporal interval array (e.g. a temporal R-R interval array).
204

Detecting a presence of one or more ectopic beats from the plurality of consecutive heartbeat related waves.
205

Correcting each interval and time value associated with each ectopic beat
206

Continued from FIG. 4A

Determining the suitability for application of each time value and each interval for a set of predetermined or dynamically set conditions.
207

Determining one or more HRV measurements from the based on data in the temporal interval array (206)
208

Combining the one or more HRV measurements with one or more additional predetermined or dynamically set input to determine when an alert is sent to one or more pre-determined parties via a real-time notification.
209

FIG. 4B

WEARABLE PHYSIOLOGICAL MONITORING AND NOTIFICATION SYSTEM BASED ON REAL-TIME HEART RATE VARIABILITY ANALYSIS

CROSS REFERENCE

This application claims priority to and is a continuation-in-part of U.S. Non-Provisional Application No. 15/004,345 filed Jan. 22, 2016, and claims priority to U.S. Provisional Patent Application No. 62/182,261, filed Jun. 19, 2015, the specification(s) of which is/are incorporated herein in their entirety by reference.

FIELD OF THE INVENTION

The present invention relates to methods, systems, and devices for real-time monitoring of heart rate variability (HRV), more particularly to HRV monitoring systems and devices that are adapted to give immediate feedback to the subject concerning their current physiological condition and any pertinent changes in their physiology.

BACKGROUND OF THE INVENTION

Heart Rate Variability ("HRV") has been widely used as a scientific measurement for monitoring the physiology of both human and animal subjects. HRV is the physiological characteristic of the variation in timing between heartbeats. The heartbeat originates in specialized tissue in the heart called the sino-atrial ("SA") node, continuously generating an electrical impulse that spreads throughout the heart muscle. This initiates the process of heart muscle contraction, a well- synchronized pump that sequentially constricts all 4 chambers of the heart (two atria and two ventricles.)

The SA node signals (approximately 100-120 impulses per minute when the heart is at rest) are regulated by the autonomic nervous system ("ANS") by inhibiting some of the electrical impulses. The net effect results in a normal resting heart rate (in healthy individuals) of about 55 to 70 beats per minute (at rest). This autonomic nervous system is the part of the nervous system that is not under conscious control. It controls the organs and systems of the body that are rhythmic, regular, and automatic such as breathing, digestion, and heart rate. There are two branches of the autonomic nervous system: sympathetic and parasympathetic.

The sympathetic nervous system provides the basal heartbeat ("HB") rhythm based on overall need. This response of the heart rate to normally encountered levels of sympathetic stimulation is modulated by parasympathetic stimulation. This heartbeat response to the parasympathetic nervous system, in contrast to the sympathetic nervous system, occurs rapidly and frequently. The deceleration of the heartbeat is almost instantaneous. It only takes 1 or 2 heartbeats to see these changes take place, slowing the heart rate.

HRV analysis can be used in both clinical and non-clinical applications for a diverse range of evaluations. In healthy individuals, the HR is variable. It fluctuates and, generally, greater variability (or HRV) correlates with better health. Higher HRV indicates a healthy autonomic nervous system, and in particular, healthy balance between the sympathetic and parasympathetic systems. A decreased HRV is an early, accurate indicator that the autonomic nervous system is out of balance. The lower the HRV, the greater the imbalance in autonomic control and the greater the likelihood of poor health, both now and in the future.

Clinical applications for HRV analysis are related to cardiac health, and are indications that are shown to directly relate to health changes with many chronic and critical health conditions. Included are, but not limited to, risk of a cardiac event, occurrence of diabetes, episodic and chronic mental health conditions, sleep apnea, SIDS, exposure to and incidence of allergic reactions.

In non-clinical applications, it has been shown that HRV is effective in indicating a variety of physiological conditions. During vigorous exercise, HRV has been shown to be a marker for entering lactate threshold or anaerobic metabolism. Further, it is shown to be an indicator of physical fatigue, exercise capacity, endurance, and overall fitness. Application has been found to be useful in assessing physiological-behavioral conditions, such as stress in trainee stock market traders and driver fatigue.

There are several ways to measure and analyze HRV. Heart rate signals are obtained through electrocardiogram ("ECG") or by pulse wave measurement called "Photoplethysmography" ("PPG"). The most accurate clinical determination of HRV is derived from measuring the duration of the intervals between contractions of the heart, called inter-beat intervals, on ECG (or EKG). In contrast, PPG is less invasive, simpler to apply, and can conveniently access capillaries in a fingertip or the earlobe. Using differential light absorption characteristics and an optical sensor, PPG detects changes in the pulse waves generated by blood flow through the microcirculation. In this way an accurate estimate of HRV can be obtained.

The present invention features a device and method for real-time HRV monitoring. The HRV systems and devices of the present invention are adapted to give immediate feedback to the subject concerning their current physiological condition and any pertinent changes in their physiology.

A few studies that outline some applications of HRV benefitting from real- time feedback include, but are not limited to, clinical applications with real time relevance such as anticipation of mood changes in patients with Bipolar Disorder, alerting the onset of infant physiological dysfunction during sleep, early warning of epileptic seizure, food allergy alerting, and sleep apnea; and non-clinical applications with real time relevance such as predicting the onset of lactate threshold in endurance athletes, warning of physiological effects of pollution, particularly volatile organic compounds ("VOCs"), alerting the onset of driver fatigue, and monitoring professionals in high stress occupations (e.g., air traffic controllers). These scenarios and many others may benefit from the accurate monitoring, analysis and real time alerting, to a relevant change in physiology as indicated by a change in HRV.

SUMMARY OF THE INVENTION

The present invention features a device providing determination, analysis, and feedback of HRV data to users on a real-time basis. In addition to the detection, analysis, and assessment of HRV data against a pre-determined application or user need, it has the ability to provide real time notifications based on the system's assessment of a user's heart rate variability and, in particular, changes in heart rate variability that may be pertinent to a specific application of this invention. This invention may further help a user to take appropriate action based on his/her specific needs.

One aspect of this invention is to provide monitoring and assessment of the impact of HRV when incorporated with other relevant factors, historical baselines, and temporal changes. Further, such temporal changes, of either or both HRV and other factors, are assessed for the providing of significant indication of occurring or impending clinical or non-clinical conditions for a user.

According to one embodiment, the invention features a wearable device for real-time detection, analysis, and application of heart rate variability (HRV). The device may comprise a chest strap integrated with one or more strap electrodes to detect a plurality of consecutive QRS waves and a battery-powered and self- contained processing circuit. The circuit may comprise a microprocessor configured to receive at least one additional input unrelated to the QRS waves detected by the strap electrodes, an ECG analog front end circuit coupled between the microprocessor and one or more one strap electrodes to provide a signal gain control to a strap electrode output such that the microprocessor receives signals with a desired amplitude, a non-volatile memory storing computer-readable instructions, and a notification means to receive a real-time notification to generate a user alert. The notification means may be a haptic indicator, an audio indicator or a visual indicator. When the computer-readable instructions are executed by the microprocessor, the microprocessor can perform operations comprising detecting a peak, a rising edge or a declining edge of an R-wave from each of the QRS waves detected; triggering an interrupt when the peak, the rising edge, or the declining edge crosses a trigger point, where the trigger point is a predetermined or dynamically adjusted value; recording a time value each time the interrupt is triggered; determining an R-R interval each time the time value is recorded; generating a temporal R-R interval array, the R-R interval array being stored within the memory and comprising a plurality of determined R-R intervals and corresponding time values; generating an HRV measurement based on the temporal R-R interval array; and comparing the determined HRV measurement to an HRV threshold and outputting a real-time notification when the HRV threshold is reached. The HRV threshold can be determined at least by the additional input unrelated to the QRS waves.

While there are many configurations and implementations of HRV analytical systems, this invention provides unique improvements and capabilities offering significant advantages over existing systems. One such improvement is the feature of employing an analog voltage comparator to detect specified characteristics of the QRS wave. This feature is critical because, traditionally, the QRS wave is sampled by an analog to digital converter ("ADC") disposed within the microcontroller and peak detection algorithms are executed by the microcontroller to determine the duration of the R-R interval, as can be seen in Scott (2010/0274308) and Kaiser (2007/0021815). This traditional approach requires additional signal processing to obtain sufficient resolution and accuracy for determining the specific heartbeat timings and, consequently, the duration of R-R intervals. The approach of the present invention provides a marked improvement over existing methods and accounts for greater capture efficacy and more responsive adaptation to unusual circumstances (e.g. a leads off situation), while maintaining the integrity of the data set used for calculation of the HRV values. By virtue of the stability provided by the device disclosed herein, it is thus sometimes unnecessary to provide for additional signal analysis and correction of the basic QRS complex waveform exclusively for the purposes of determining the R-R timing.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DEFINITIONS

As used herein, the trigger point is the voltage level at which the R-wave triggers an interrupt.

As used herein, the HRV threshold is the level the selected HRV measurement crosses in order to generate an alert.

As used herein, the R-R interval is the time between two consecutive R- waves (usually expressed in milliseconds).

BRIEF DESCRIPTION OF THE DRAWINGS

FIGS. 3A-3D are a table showing exemplary HRV measurements and associated sample applications involving each specific measurement. Each one of these calculations yields a single measurement. In steady state conditions, these measurements remain fairly constant, but can change with changes in the physiology of the subject. For example, if there is a rapid increase in the value of HF preceding an epileptic seizure, or during exercise, the subject crosses his or her lactate threshold as the value of SD1 drops below 3.0.

One skilled in the art will recognize that various implementations and embodiments of the invention may be practiced in accordance with the specification. All of these implementations and embodiments are intended to be included within the scope of the invention.

DETAILED DESCRIPTION OF THE INVENTION

In the following description, for the purpose of explanation, specific details are set forth in order to provide an understanding of the present invention. The present invention may be practiced without some or all of these details. The embodiments of the present invention described below may be incorporated into a number of different electrical components, circuits, devices, and systems. Structures and devices shown in schematic diagrams are illustrative of exemplary embodiments and are not to be used as a pretext by which to obscure broad teachings of the present invention.

When the specification makes reference to "one embodiment" or to "an embodiment", it is intended to mean that a particular feature, structure, characteristic, or function described in connection with the embodiment being discussed is included in at least one contemplated embodiment of the present invention. Thus, the appearance of the phrase, "in one embodiment," in different places in the specification does not constitute a plurality of references to a single embodiment of the present invention.

The present invention features a wearable device (101) for real-time detection, analysis, and application of heart rate variability (HRV). Referring now to FIGS. 1-4B, in some embodiments the device (101) is compact, battery-powered, wearable, and portable. It may comprise a chest strap (120) and a battery-powered, self-contained, processing circuit (110). The processing circuit (110) may comprise a memory (308) coupled to a microprocessor (301). In one embodiment, one or more strap electrodes (307) may be integrated into the chest strap (120) and configured to detect a plurality of consecutive QRS waves. In alternate embodiments, the microprocessor (301) may be a microcontroller, a digital signal processing (DSP) circuit, a programmable logic circuit, a CPU, etc. The memory (308) may be a non-volatile repository storing computer readable logic/control codes (or instructions) and computer generated data. In some embodiments, the microprocessor (301) and the memory (308) are integrated into one integrated circuit.

Figure 2:
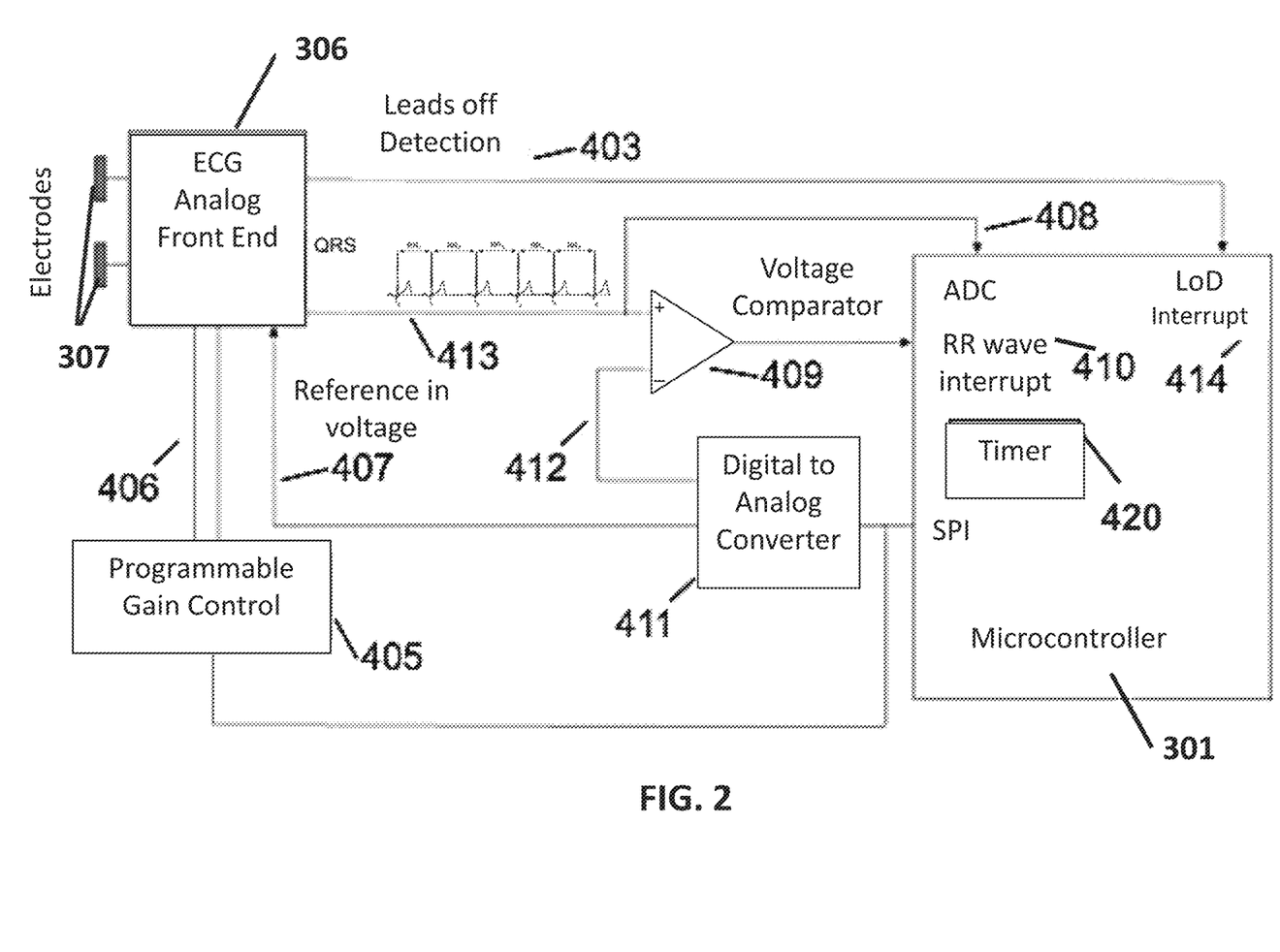
FIG. 2 shows a detailed block diagram of the front-end detection in a HRV device of the present invention.
Figure 3A:
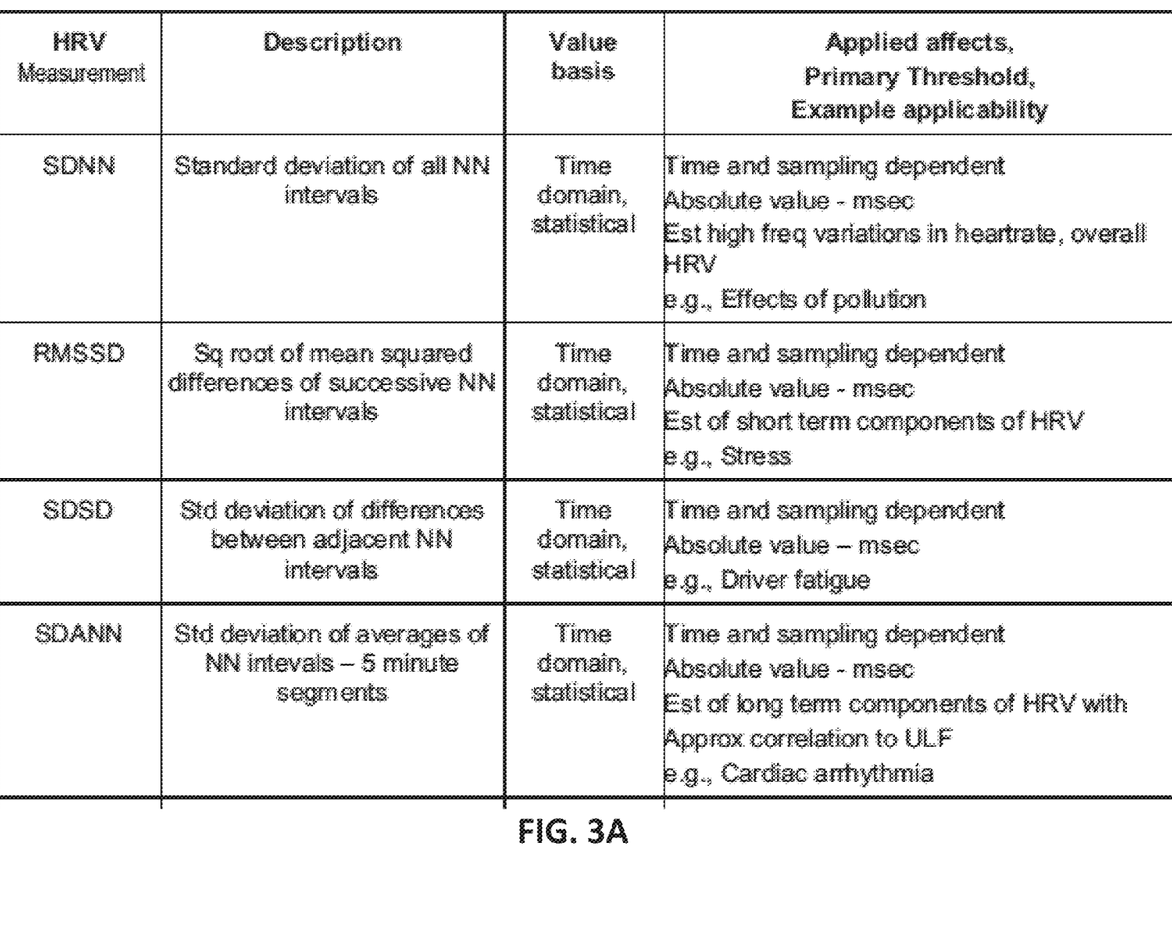
Figure 3B:
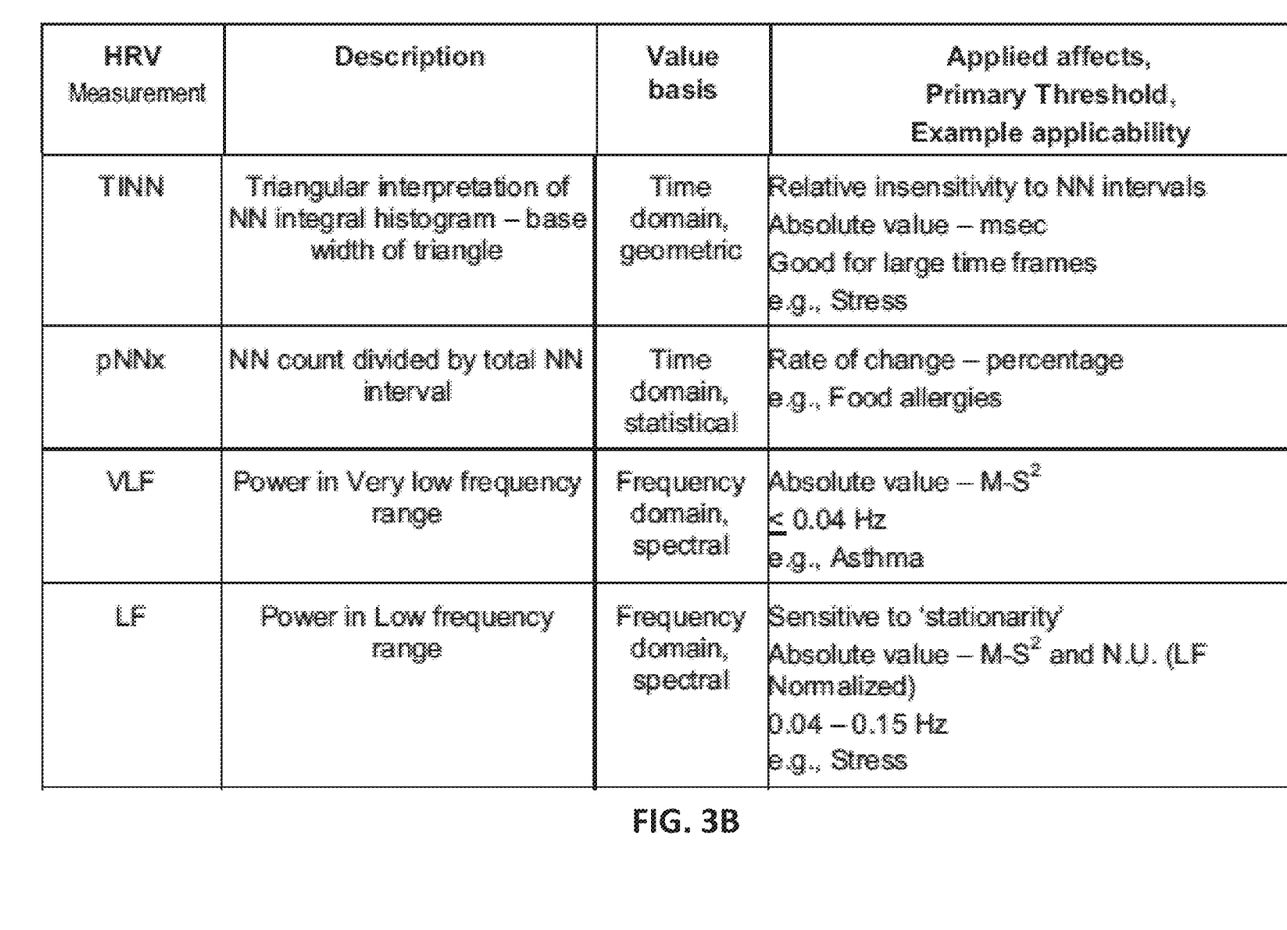
Figure 3C:
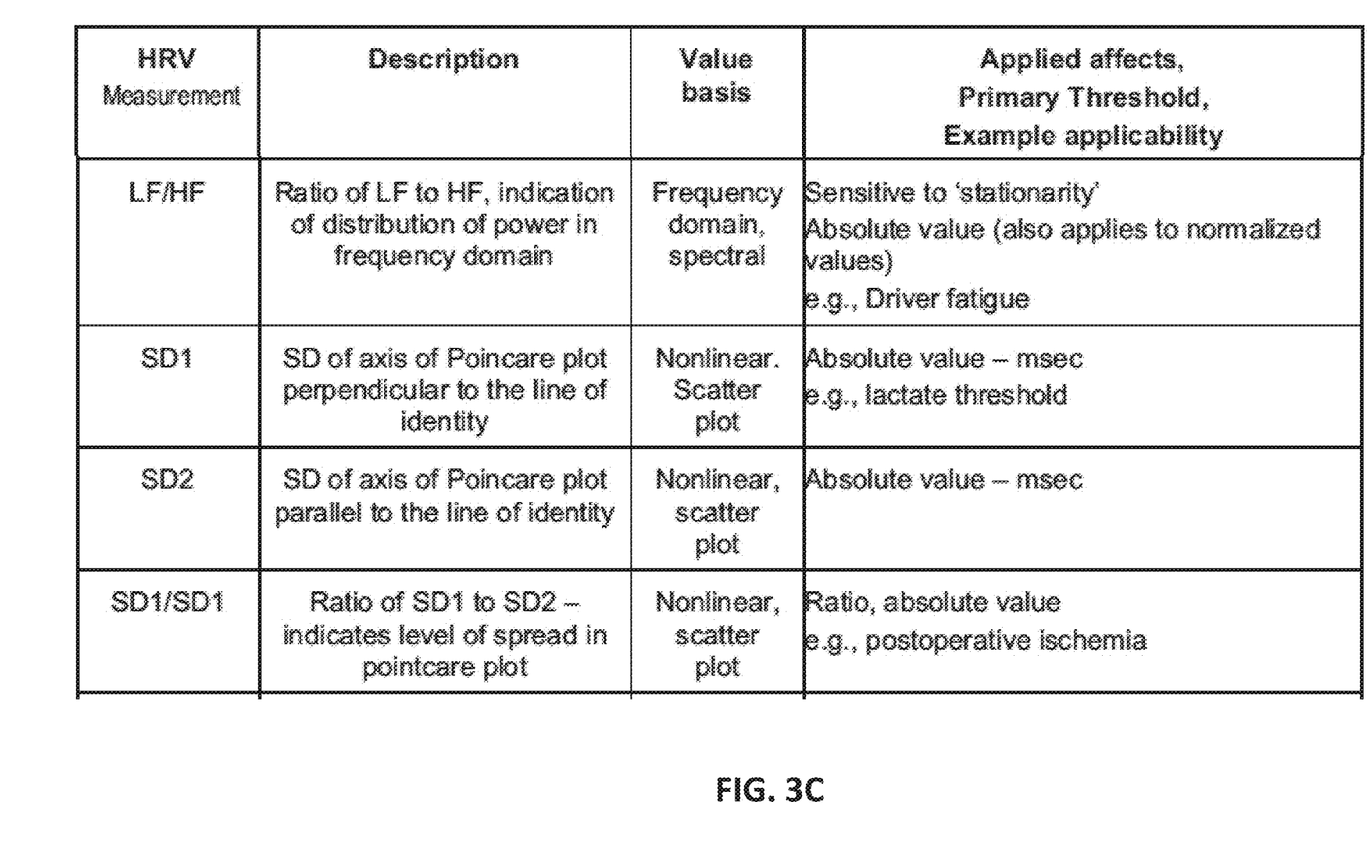
Figure 3D:
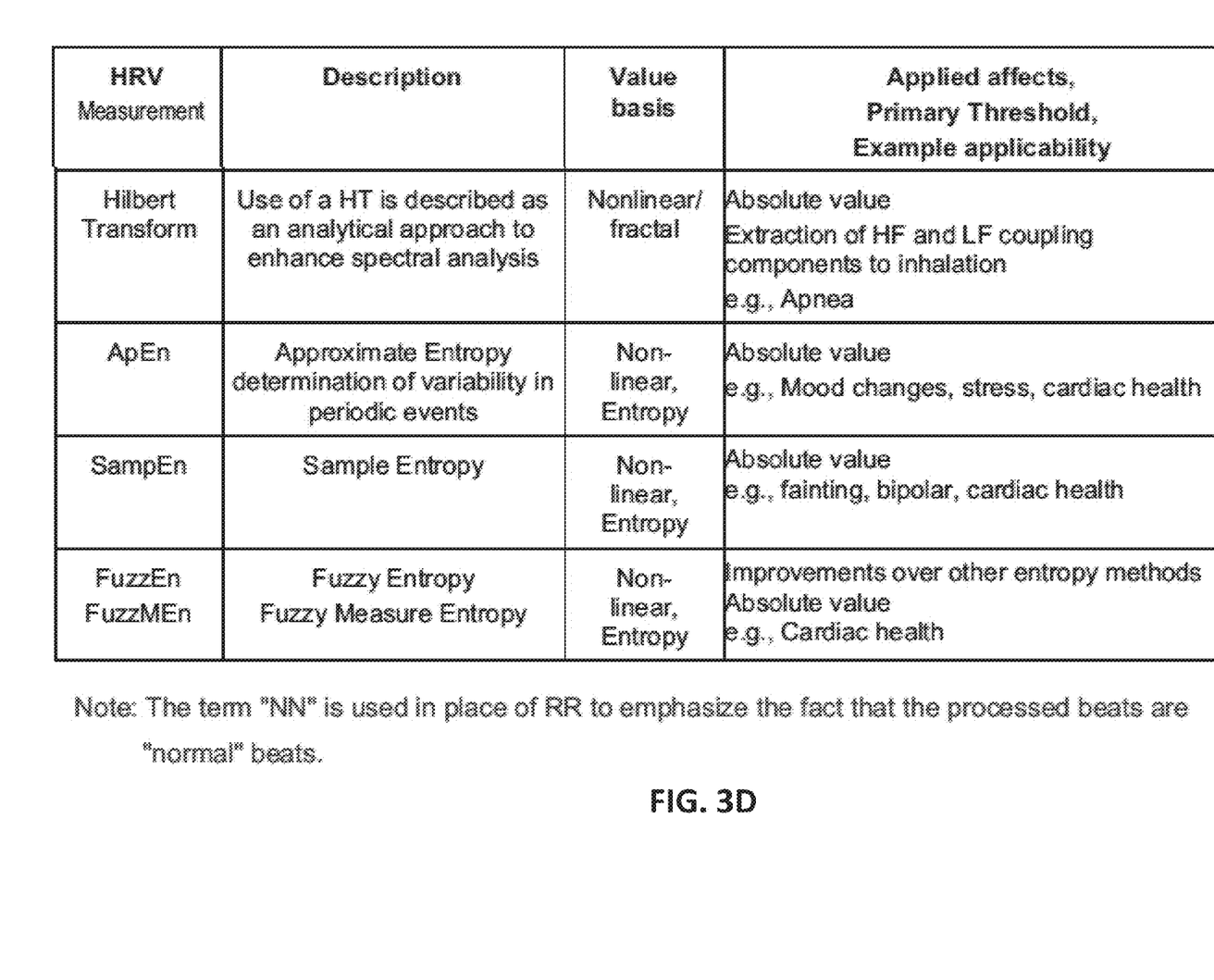
Figure 4A:
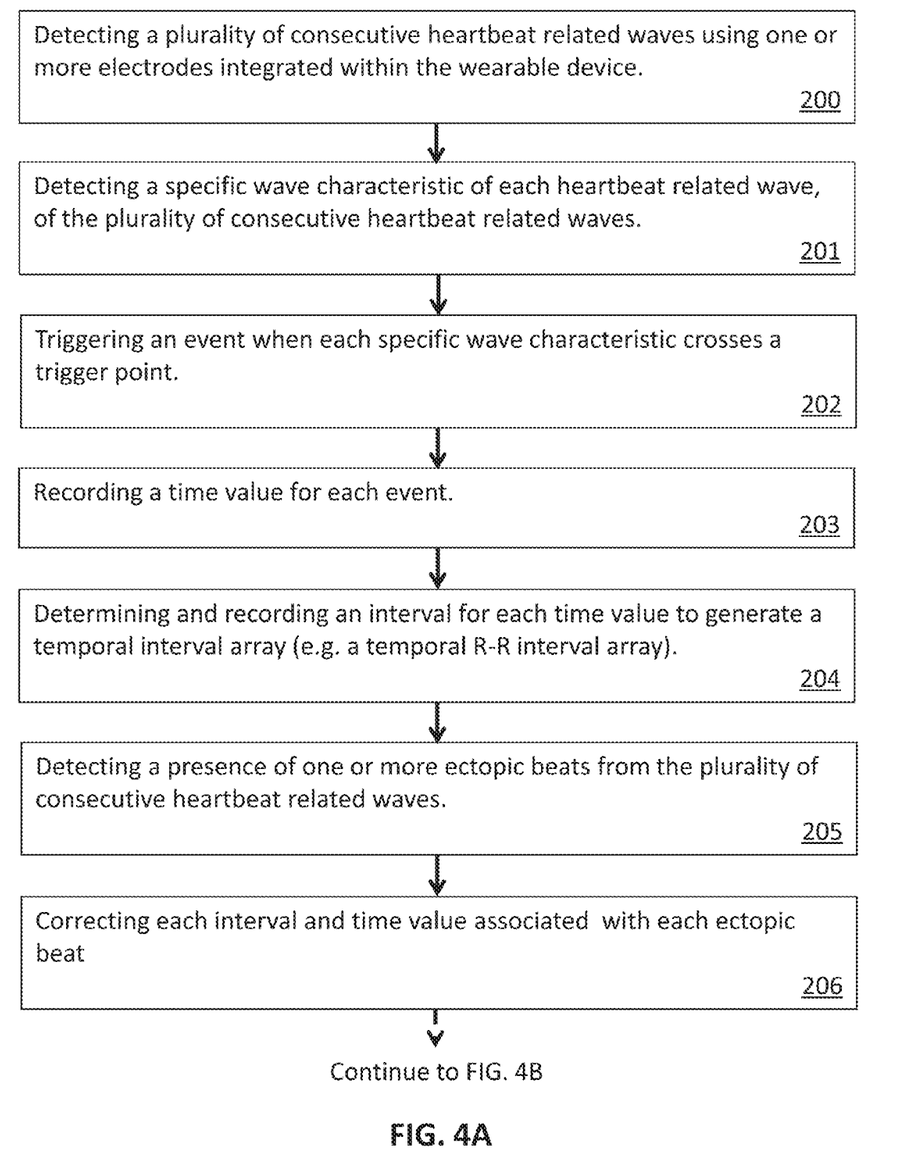
FIGS. 4A-4B are a logic flow diagram for an embodiment of the method of the present invention.
Figure 4B:
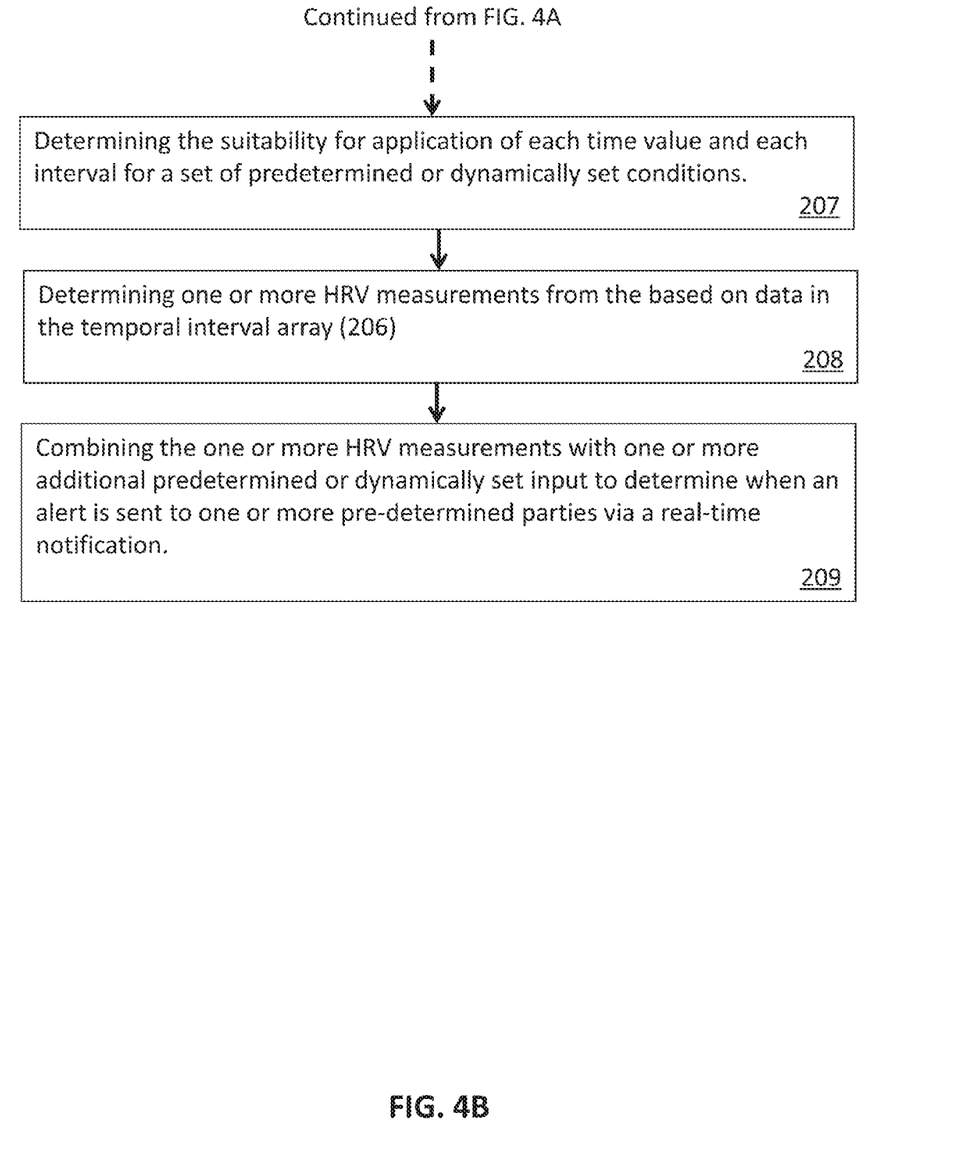

In further embodiments, the processing circuit (110) may comprise an electrocardiogram ("ECG") analog front end ("AFE") integrated circuit (306) coupled between the microprocessor (301) and the one or more strap electrodes (307). The AFE circuit (306) may be configured to provide a necessary signal gain control to one or more output signals emerging from the one or more strap electrodes (307) so that said signals exhibit a desired amplitude before transmission to the microprocessor (301). In additional embodiments, the microprocessor (301) may execute computer-readable instructions stored in the non-volatile memory (308), causing the microprocessor (301) to perform operations such as detecting the rising edge, the peak, and/or the declining edge of an R-wave from each QRS wave. An event may be triggered to capture and record a time value when the rising edge, the declining edge, and/or the peak of each R-wave crosses a trigger point. In one embodiment, the trigger point may be a predetermined value or a dynamically adjusted value. In another embodiment, the event may be a time capture, a real-time clock value capture, or an independent timer value capture. Further, an R-R interval may be determined and recorded for each time value to generate a temporal R-R interval array, which is stored in the non-volatile memory (308).

The plurality of consecutive heart beat related waves, each time value, and each interval may then be analyzed for suitability of use for HRV related applications. To accomplish this analysis, additional operations executed by the microprocessor (301) may include determining a presence of one or more ectopic beats from the plurality of consecutive QRS waves and correcting the R-R interval and time value associated with each ectopic beat to produce corrected R-R intervals and time values. Correction may be accomplished by comparing an R-R interval and time value of an ectopic beat to a predetermined value and replacing the R-R interval and time value with a calculated R-R interval value and a calculated time value if the R-R interval and time value exceed the predetermined value. One or more HRV measurements may then be determined based on corrected R-R intervals and time values. Non-limiting examples of methods for generating the calculated R-R interval values and the calculated time values comprise: standard deviation of normal to normal R-R intervals ("SDNN"), root mean square of successive N-N interval differences ("RMSSD"), standard deviation of successive differences ("SDSD"), standard deviation of averages of N-N intervals ("SDANN"), triangular interpolation of N-N interval histogram ("TINN"), NN count divided by total NN interval ("pNNx"), Hilbert Transform, approximate entropy ("ApEn"), sample entropy ("SampEn"), fuzzy entropy ("FuzzEn"), fuzzy measure entropy ("FuzzMEn"), or spectral HRV measurements including: power in very low frequency ("VLF"), power in low frequency ("LF"), power in high frequency ("HF"), a ratio of LF to HF, standard deviation of Poincare plot perpendicular to a line of identity ("SD1"), standard deviation of axis of Poincare plot parallel to the line of identity ("SD2"), or a ratio of SD1 to SD2 (see FIGS. 3A-3D).

In supplementary embodiments, the one or more HRV measurements are combined with one or more additional predetermined or dynamically set input to determine when an alert is sent to one or more pre-determined parties via a real-time notification. These predetermined or dynamically set inputs may comprise: respiration rate, blood pressure value, body temperature, level of physical motion, heart rate, a pre-determined condition marker (e.g. a blood sugar level), a pre-existing condition specification, or a level of electrodermal activity. In some embodiments, the pre-existing condition specification may comprise: sleep apnea, physical exertion, tendency for epileptic seizure, diabetes, or stress. The real time notification may be a haptic indicator, an auditory indicator, or a visual indicator disposed on the device (100).

In additional embodiments, the processing circuit (110) may also comprise an onboard threshold set potentiometer (or adjusting switch) (305) coupled to the microprocessor (301). The potentiometer (or adjusting switch) (305) may receive user inputs for the microprocessor (301) to determine HRV measurements accordingly. The user inputs may be an exercise status input, a health status input, etc. The processing circuit (110) may further comprise an optional connector (304) coupled to the microprocessor (301), which provides the real time notification to the user through the connector (304) and an external earpiece coupled to the connector (304).

Figure 1:
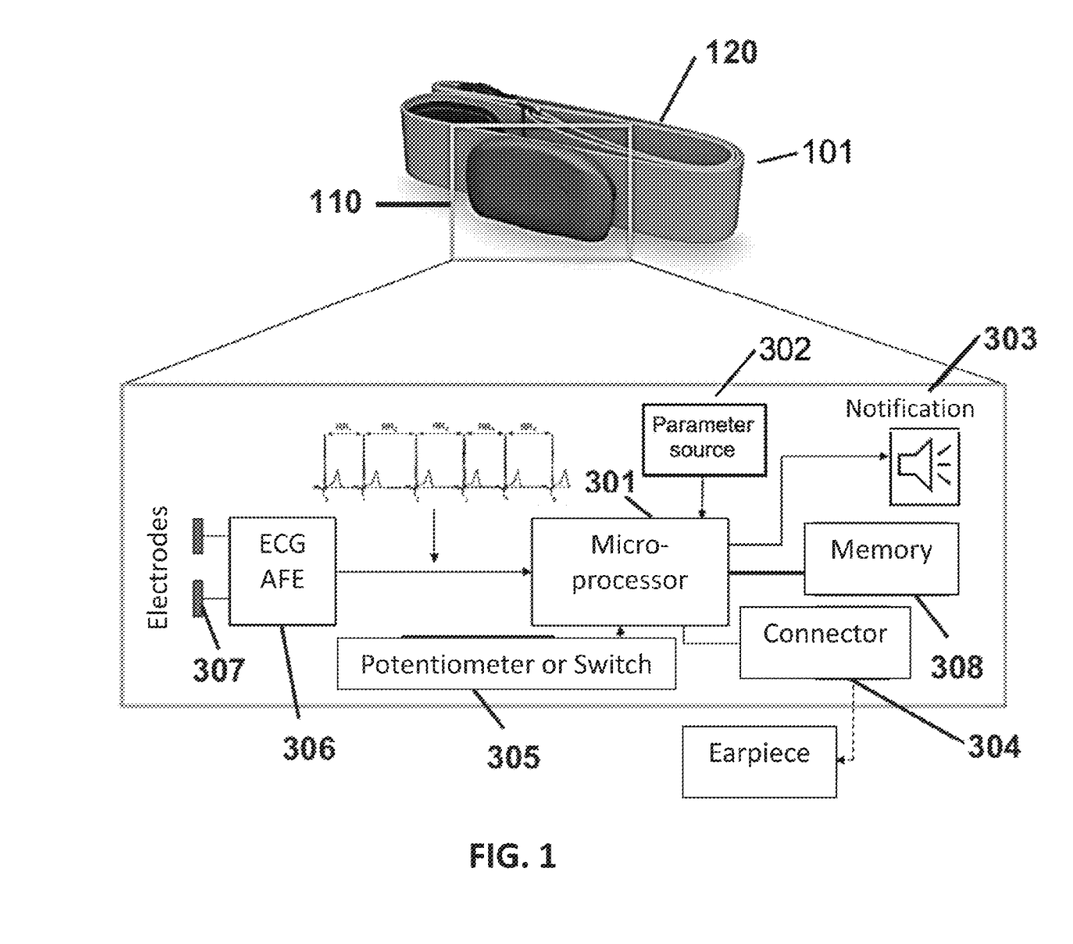
FIG. 1 shows an example of a wearable HRV monitoring device (e.g., compact, integrated, portable, battery powered, etc.).

Although the wearable device (100) is shown in FIG. 1 with a chest strap (120), it is understood that other variations may be applicable to the device as well. Such variations could be in the form of, but not limited to, a watch, self-adhesive patch, armband, bra, belt, etc. The strap electrodes (307) may be integrated into the chest strap (120) such that the electrodes may be disposed at the right position when the device is worn by the user.

FIG. 2 shows a detail schematic view of the front end detection in an embodiment of the present invention. Two chest strap electrodes (307) are coupled to the AFE circuit (306). A non-limiting example of the AFE circuit is an Analog chip AD8232. In some embodiments, the AFE circuit (306) contains an internal amplifier to output a conditioned QRS signal (413) comprising multiple QRS complexes to a voltage comparator (409). In other embodiments, the AFE circuit (306) is configured to output a Leads off Detection (LoD) signal (403) when one or both of the chest strap electrodes (307) have been disconnected from the user, thereby compromising the integrity of the ECG data. The LoD signal (403) may be coupled to a LoD interrupt input pin (414) of a microcontroller (301). The microcontroller (301) can then activate a 'Fast Restore' feature of the AFE circuit (306) in order to reset the internal filters so that the AFE circuit (306) is reconfigured to immediately detect a new R-wave. The microcontroller (301) may also use this information to identify, reject, or correct the resulting erroneous R-R interval data. Additionally, an internal timer (420) in the microprocessor (301) can monitor the LoD (403) and in the event that the leads are off longer than a threshold (a long period of time, such as 15 seconds), enable the microcontroller (301) to enter a low power sleep mode, assuming that the user has removed the device.

In some embodiments, in order to optimize the performance of the AFE circuit (306), the microcontroller (301) may adjust the output gain of the AFE circuit (306) to minimize saturation via a programmable gain control (405).

Additionally, the microcontroller (301) can adjust the reference level of the AFE circuit instrumentation amplifier (407) in order to optimize the average level of the R pulse baseline. This can be achieved by monitoring and averaging the QRS signal (408) using an ADC and adjusting the reference-in voltage (407) to maintain a very stable baseline.

Traditionally, the QRS signal is sampled by an analog to digital converter within the microcontroller and peak detection algorithms are executed in the microcontroller to determine the duration of the R-R interval. This approach requires signal processing to obtain sufficient resolution and accuracy in determining the specific heartbeat timings and consequently duration of the R-R intervals.

It is an object of this invention, in some embodiments, to employ an analog voltage comparator (409) to detect a specific desired wave characteristic and use that detection event to directly trigger an interrupt (410) on the signal processor. The specific wave characteristic may be, but is not limited to, the steep rising edge of the R-wave, the peak of the R-wave, or the steep declining edge of the R-wave complex. Each may be used to directly trigger an interrupt on the microcontroller, with each embodiment having its own characteristics. Combinations of specific wave characteristics are as well possible and it is not meant to, within this invention, to limit the use of and the combinations of wave characteristics for this detection.

A digital to analog converter ("DAC") (411) connected to the microcontroller may be used to actively set (or dynamically adjust) the threshold (412) based on the magnitude variation of the R-wave between different users or historic data stored within the memory (308). The threshold (412) is used to compare to the conditioned QRS signal (413) by voltage comparator (409). When the conditioned QRS signal (413) reaches the threshold (412), the voltage comparator (409) outputs an interrupt signal (410) to the microcontroller (301). While FIG. 2 shows discrete external components, this is not meant to limit a desired embodiment, as this capability may be discrete or integrated into the microcontroller. It is herein provided for greater clarity of explanation.

The interrupt (410) is used by the microcontroller (301) to obtain a time value from a timer (420) that was reset on the last occurrence of a valid interrupt. The obtained time value is then the most recent R-R interval. This direct and temporal determination of the R-R interval for HRV provides a highly accurate determination of the R-R interval while lowering power requirements, computational requirements, memory storage and timing limitations for computationally intense digitizing/analysis methods. The obtained R-R interval array is stored within the memory (308) for further analysis and history data output when applicable. The precision and accuracy of this determination is only limited by the timing capabilities of the microcontroller (301) and is often provided with sub-millisecond resolution and accuracy.

By virtue of the stability provided by the above described technique, it is sometimes unnecessary to provide for additional signal analysis and correction of the basic QRS complex waveform exclusively for the purposes of determining the R- R timing. Even with this stability, there are advantages to enhanced error detection, improved noise rejection and verification of the specific wave characteristics expected. It is a further object of this invention to enable enhancements in these validations of the base R-R interval determination.

This additional analysis is valuable to provide for the confirmation of viable heartbeat (HB) and HRV data and to determine consistency and viability of the assessment.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although as described in the preferred embodiment of the present invention, it will be readily apparent to those skilled in the art that modifications may be made thereto which do not exceed the scope of the appended claims. Therefore, the scope of the invention is only to be limited by the following claims. Reference numbers recited herein are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for real-time detection, analysis, and application of heart rate variability (HRV) using a wearable device, the method comprising:
   (a) detecting a plurality of consecutive heartbeat related waves using one or more electrodes integrated within the wearable device (200);
   (b) detecting a specific wave characteristic of each heartbeat related wave, of the plurality of consecutive heartbeat related waves (201);
   (c) triggering an event when each specific wave characteristic crosses a trigger point (202), wherein the event is based on one or more inputs unrelated to the plurality of consecutive heartbeat related waves,
   (d) recording a time value for each event triggered (203);
   (e) determining and recording an interval for each time value to generate a temporal interval array (204);
   (f) analyzing the plurality of consecutive heart beat related waves, each time value, and each interval for suitability of use for HRV related applications, said analysis comprises:
      (i) detecting a presence of one or more ectopic beats from the plurality of consecutive heartbeat related waves (205);
      (ii) correcting each time value and interval associated with each ectopic beat (206);
      (iii) determining the suitability for application of each time value and each interval for a set of predetermined or dynamically set conditions (207); and
      (iv) determining one or more HRV measurements based on data in the temporal interval array (208); and
   wherein the one or more HRV measurements are combined with one or more additional predetermined or dynamically set input to determine when an alert is sent to one or more pre-determined parties via a real-time notification (209).

2. The method of claim 1, wherein the one or more HRV measurements are time dependent HRV values.

3. The method of claim 1, wherein the event comprises a time capture, a real-time clock value capture, or an independent timer value capture.

4. The method of claim 2, wherein the temporal interval array is a temporal R-R interval array.

5. The method of claim 4, wherein corrected R-R intervals and time values are generated by correcting each R-R interval and time value associated with each ectopic beat, said correction comprises:
   (a) comparing an R-R interval and time value of an ectopic beat to a predetermined value,
   (b) replacing the R-R interval and time value with a calculated R-R interval value and a calculated time value if the R-R interval and the time value exceed the predetermined value, and
   (c) repeating (a) and (b) for each R-R interval and time value associated with an ectopic beat.

6. The method of claim 5, wherein the one or more HRV measurements are determined based on corrected R-R intervals and corrected time values.

7. The method of claim 5, wherein the method of generating the calculated R-R interval value and the calculated time value comprises: standard deviation of normal to normal R-R intervals ("SDNN"), root mean square of successive N-N interval differences ("RMSSD"), standard deviation of successive differences ("SDSD"), standard deviation of averages of N-N intervals ("SDANN"), triangular interpolation of N-N interval histogram ("TINN"), NN count divided by total NN interval ("pNNx"), Hilbert Transform, approximate entropy ("ApEn"), sample entropy ("SampEn"), fuzzy entropy ("FuzzEn"), fuzzy measure entropy ("FuzzMEn"), or spectral HRV measurements including: power in very low frequency ("VLF"), power in low frequency ("LF"), power in high frequency ("HF"), a ratio of LF to HF, standard deviation of Poincare plot perpendicular to a line of identity ("SD1"), standard deviation of axis of Poincare plot parallel to the line of identity ("SD2"), or a ratio of SD1 to SD2.

8. The method of claim 1, wherein the one or more predetermined or dynamically set inputs comprise: respiration rate, blood pressure value, body temperature, level of physical motion, heart rate, a pre-determined condition marker, a pre-existing condition specification, or a level of electrodermal activity.

9. The method of claim 8, wherein the pre-determined condition marker comprises a blood sugar level.

10. The method of claim 8, wherein the pre-existing condition specification comprises: sleep apnea, physical exertion, tendency for epileptic seizure, diabetes, or stress.

11. The method of claim 1, wherein the real-time notification comprises: a haptic indicator, an auditory indicator, or a visual indicator.

12. A wearable device (100) for real-time detection, analysis, and application of heart rate variability (HRV), the device comprising:
   (a) a chest strap (120) or wearable article integrated with one or more strap electrodes (307) to detect a plurality of consecutive QRS waves; and
   (b) a battery-powered, self-contained processing circuit (110) comprising:
      (i) a microprocessor (301), operatively coupled to the one or more strap electrodes (307), configured to receive one or more additional inputs unrelated to the plurality of consecutive QRS waves detected by the one or more strap electrodes (307);
      (ii) an electrocardiogram ("ECG") analog front end ("AFE") circuit (306), coupled between the microprocessor (301) and the one or more strap electrodes (307), providing a signal gain control to an output of the one or more strap electrodes (307) so that the output has a desired amplitude before transmission to the microprocessor (301);
      (iii) a non-volatile memory (308), operatively coupled to the microprocessor (301), storing computer-readable instructions which, when executed by the microprocessor (301), cause the microprocessor (301) to perform operations comprising:
         (A) detecting a rising edge, a peak, or a declining edge of an R- wave from each QRS wave;
         (B) triggering an event when the rising edge, the declining edge, or the peak of each R-wave crosses a trigger point, wherein the trigger point is a predetermined value or a dynamically adjusted value;
         (C) recording a time value for each event triggered;
         (D) determining and recording an R-R interval for each time value to generate a temporal R-R interval array, which is stored in the non-volatile memory (308);
         (E) analyzing the plurality of consecutive heart beat related waves, each time value, and each interval for suitability of use for HRV related applications, said analysis comprises:
            (I) detecting a presence of one or more ectopic beats from the plurality of consecutive heartbeat related waves;
            (II) correcting each time value and interval associated with each ectopic beat;
            (III) determining the suitability for application of each time value and each interval for a set of predetermined or dynamically set conditions; and
            (IV) determining one or more HRV measurements based on data in the temporal R-R interval array; and
wherein the one or more HRV measurements are combined with one or more additional predetermined or dynamically set input to determine when an alert is sent to one or more pre-determined parties via a real-time notification.

13. The device (101) of claim 12, wherein the event comprises a time capture, a real-time clock value capture, or an independent timer value capture.

14. The device (101) of claim 12, wherein corrected R-R intervals and time values are generated by correcting each R-R interval and time value associated with each ectopic beat, said correction comprises:
   (a) comparing an R-R interval and time value of an ectopic beat to a predetermined value,
   (b) replacing the R-R interval and time value with a calculated R-R interval value and a calculated time value if the R-R interval and the time value exceed the predetermined value, and
   (c) repeating (a) and (b) for each R-R interval and time value associated with an ectopic beat.

15. The device (101) of claim 14, wherein the one or more HRV measurements are determined based on corrected R-R intervals and time values.

16. The device (101) of claim 14, wherein the method of generating the calculated R- R interval value and the corrected time value comprises: standard deviation of normal to normal R-R intervals ("SDNN"), root mean square of successive N-N interval differences ("RMSSD"), standard deviation of successive differences ("SDSD"), standard deviation of averages of N-N intervals ("SDANN"), triangular interpolation of N-N interval histogram ("TINN"), NN count divided by total NN interval ("pNNx"), Hilbert Transform, approximate entropy ("ApEn"), sample entropy ("SampEn"), fuzzy entropy ("FuzzEn"), fuzzy measure entropy ("FuzzMEn"), or spectral HRV measurements including: power in very low frequency ("VLF"), power in low frequency ("LF"), power in high frequency ("HF"), a ratio of LF to HF, standard deviation of Poincare plot perpendicular to a line of identity ("SD1"), standard deviation of axis of Poincare plot parallel to the line of identity ("SD2"), or a ratio of SD1 to SD2.

17. The device (101) of claim 12, wherein the one or more predetermined or dynamically set inputs comprise: respiration rate, blood pressure value, body temperature, level of physical motion, heart rate, a pre-determined condition marker, a pre-existing condition specification, or a level of electrodermal activity.

18. The device (101) of claim 17, wherein the pre-determined condition marker comprises a blood sugar level.

19. The device (101) of claim 17, wherein the pre-existing condition specification comprises: sleep apnea, physical exertion, tendency for epileptic seizure, diabetes, or stress.

20. The device (101) of claim 12, wherein the real-time notification (303) comprises a haptic indicator, an auditory indicator, or a visual indicator disposed on the device (101).

* * * * *